United States Patent [19]
Gale et al.

[11] Patent Number: 5,198,223
[45] Date of Patent: * Mar. 30, 1993

[54] TRANSDERMAL FORMULATIONS, METHODS AND DEVICES

[75] Inventors: Robert M. Gale; Diane E. Nedberge, both of Los Altos; Linda E. Atkinson, Portola Valley, all of Calif.

[73] Assignee: Alza Corporation, Palo Alto, Calif.

[ * ] Notice: The portion of the term of this patent subsequent to Jun. 6, 2009 has been disclaimed.

[21] Appl. No.: 848,578

[22] Filed: Mar. 9, 1992

Related U.S. Application Data

[63] Continuation-in-part of Ser. No. 605,726, Oct. 29, 1990, Pat. No. 5,122,382.

[51] Int. Cl.$^5$ .............................................. A61F 13/00
[52] U.S. Cl. .................................. 424/449; 424/447; 424/448; 514/772.4; 530/399
[58] Field of Search ............... 424/449, 448, 447, 443; 530/399; 514/772.4

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 3,710,795 | 1/1973 | Higuchi et al. | 128/260 |
| 3,800,038 | 3/1974 | Rudel | 424/433 |
| 3,948,262 | 4/1976 | Zaffaroni | 128/260 |
| 4,136,145 | 1/1979 | Fuchs et al. | 264/164 |
| 4,144,317 | 3/1979 | Higuchi et al. | 424/21 |
| 4,286,592 | 9/1981 | Chandrasekaran | 128/260 |
| 4,291,014 | 9/1981 | Keith et al. | 424/28 |
| 4,314,557 | 2/1982 | Chandrasekaran | 128/260 |
| 4,379,454 | 4/1983 | Campbell et al. | 604/897 |
| 4,438,139 | 3/1984 | Keith et al. | 424/28 |
| 4,568,343 | 2/1986 | Leeper et al. | 604/896 |
| 4,624,665 | 11/1986 | Nuwayser | 604/307 |
| 4,746,515 | 5/1988 | Cheng et al. | 424/449 |
| 4,816,258 | 3/1989 | Nedberge et al. | 424/448 |
| 4,818,540 | 4/1989 | Chien et al. | 424/448 |
| 4,863,738 | 9/1989 | Taskovich | 424/449 |
| 4,906,169 | 3/1990 | Chien et al. | 424/448 |
| 4,913,905 | 4/1990 | Fankhauser et al. | 424/449 |
| 4,994,278 | 2/1991 | Sablotsky et al. | 424/449 |

FOREIGN PATENT DOCUMENTS

| | | |
|---|---|---|
| 15323/88 | 10/1988 | Austria . |
| B1-0013606 | 7/1980 | European Pat. Off. . |
| A2-013606 | 7/1980 | European Pat. Off. . |
| 0165696 | 12/1985 | European Pat. Off. . |
| 3836862 | 5/1990 | Fed. Rep. of Germany . |
| WO90/0043-97 | 5/1990 | PCT Int'l Appl. . |
| WO9006736 | 6/1990 | PCT Int'l Appl. . |

OTHER PUBLICATIONS

Chemical Abstract, vol. 113, No. 17, Oct. 22, 1990, (Columbus, Ohio, US) M. Laurikka-Routti et al.: "A contraceptive vaginal ring releasing ethinyl estradio and the progestin ST-1435: bleeding control, serum steroid concentrations, serum lipids and serum chemistry".

Chemical Abstract, vol. 102, No. 21, May 27, 1985, (Columbus, Ohio, US) Viveca Odlind et al.: "ST-1435. Development of an implant".

Knepp et al., "Transermal Drug Delivery: Problems and Possibilities," CRC Critical Reviews in Therapeutic Drug Carrier Systems, vol. 4, Issue 1, pp. 13-37 (1987).

Pannatier, et al., "The Skin as a Drug Metabilizing Organ," Drug Metabolism Reviews, vol. 8, No. 2, pp. 319-343 (1978).

Näthke, et al., "Transdermal Delivery of Levonorgest-

(List continued on next page.)

Primary Examiner—Thurman K. Page
Assistant Examiner—Leon R. Horne
Attorney, Agent, or Firm—Jacqueline S. Larson; Edward L. Mandell; Steven F. Stone

[57] ABSTRACT

The present invention provides compositions and methods for the transdermal administration of a therapeutically effective amount of a synthetic 19-nor-progesterone (ST-1435) and an estrogen, in combination, together with, optionally, a suitable permeation enhancer.

21 Claims, 3 Drawing Sheets

OTHER PUBLICATIONS trel," Proceedings of 13th International Symposium on Controlled Release of Bioactive Materials, Chaudry and Thies, eds., The Controlled Release Society, Inc., pp. 29-30 (1986).

Friend, David R., "Transdermal Delivery of Levonorgestrel," Medicianl Research Reviews, vol. 11, No. 1, 049-080 (1991).

Haukkamaa, Maijä; Laurikka-Routti, Marjut and Heikinheimo, Oskari, "Transdermal Absorption of the Progestin ST-1435: Therapeutic Serum Steroid Concentrations and High Excretion of the Steroid in Saliva," Contraception, vol. 44, No. 3, pp. 269-276 (1991).

TRANSDERMAL FORMULATIONS, METHODS AND DEVICES

REFERENCE TO RELATED APPLICATION

This application is a continuation-in-part of application Ser. No. 07/605,726, now U.S. Pat. No. 5,122,382 filed on Oct. 29, 1990.

FIELD OF THE INVENTION

This invention relates to transdermal drug delivery. More particularly, this invention relates to the transdermal delivery, in a combination, of ST-1435 and estrogens, such as ethinyl estradiol, at therapeutically effective rates.

BACKGROUND OF THE INVENTION

The transdermal route of parenteral delivery of drugs provides many advantages, and transdermal systems for delivering a wide variety of drugs or other beneficial agents are described in U.S. Pat. Nos. 3,598,122, 3,598,123, 4,379,454, 4,286,592, 4,314,557 and 4,568,343, for example, all of which are incorporated herein by reference.

ST-1435 is a known synthetic 19-nor-progesterone (16-methylene17-α-acetoxy-19-nor-4-pregnene-3,20-dione). Both in animals and in humans, ST-1435 is very potent when given parenterally, whereas it is practically inactive when given orally. Because of this, ST-1435 has been used as a subcutaneous implant.

Oral combination pills, implants and intrauterine devices for purposes of contraception have been well documented for their problems such as inconvenience and side effects. Transdermal delivery of contraceptives as disclosed herein is an attempt to eliminate or reduce those problems.

However, there are many factors which affect the suitability of an active agent for transdermal administration. These are discussed at length in Knepp et al., "Transdermal Drug Delivery: Problems and Possibilities," CRC Critical Reviews in Therapeutic Drug Carrier Systems, Vol. 4, Issue 1 (1987). When it is desired to deliver more than one active agent from a single transdermal delivery device, the problems associated with achieving a workable multi-drug transdermal device with any specific combination of drugs are even more complex and difficult and can often prove to be insurmountable.

Conventional dosage forms such as tablets or injections can administer a combination of two or more active agents, each at their appropriate dose, merely by appropriate selection of the amount of each agent included in the dosage form. In transdermal delivery devices, however, the total dosage of each agent is not established by the amounts of each agent that are in the device. Instead, the total dosage of each agent is the product of its average transdermal administration rate ($\mu$g/hr) and the time over which the device is applied, and the average administration rate of an agent from a transdermal delivery device is determined primarily by a combination of factors other than the amount of the agent present in the device.

In order for a transdermal delivery device to be able to administer two or more agents from a common reservoir over the same period of time, the relative permeabilities of each of the agents through the skin and the components of the device must bear the same relationship as their relative dosage or administration rate. Thus, for example, if the dosage of each agent were the same, for example 15 $\mu$g/day, each agent would have to have the same overall permeability. If, however, one agent were to be delivered at a dosage of 20 $\mu$g/day and the other at 1 $\mu$g/day, the overall permeability of one would have to be 20 times greater than that of the other.

The situation becomes even more complicated if permeation enhancers are required to increase the inherent permeability of the skin to one or more of the agents being delivered. Identifying a permeation enhancer which has the ability to selectively increase the permeation of the skin to only one agent or to relatively increase the permeability of the skin to two or more agents in the required relationship could often provide an insurmountable obstacle for any specific combination of agents.

If the problems associated with obtaining the desired relative administration rates of the individual agents to the skin can be solved, other factors remain to be dealt with. The agents individually, in combination with each other, or in combination with a permeation enhancer must not cause undue irritation or sensitization when applied topically under occlusion. Materials which individually are not irritating or sensitizing may become so when presented to the skin in combination with each other.

Further, the skin has been recognized as the largest metabolizing organ of the body, larger even than the liver. See, A. Pannatier, et al, "The Skin as a Drug Metabolizing Organ," Drug Metabolism Reviews, Vol. 8, No. 2, pp 319–343 (1978). Skin can metabolize agents administered transdermally into inactive or potentially harmful metabolites. Thus, it is necessary that the rate at which each agent is metabolized by the skin and the metabolites produced do not prevent the safe and therapeutically effective transdermal administration of each agent into the bloodstream at the desired administration rate.

Assuming these obstacles can be overcome, it is also important that the agent binding capacity of the skin for each of the agents have the proper relationship. Before transdermal administration of an agent into the bloodstream can commence at a steady state rate, the capacity of the skin below the device to bind the agent must be saturated. The time required to achieve this steady state rate is known as the "lag time" and is a function of the rate at which the agent permeates into the skin and the binding capacity of the skin for that agent. In order for the lag time for both agents to be the same, there must be an inverse relationship between each agent's administration rate and the binding capacity of the skin for each agent.

Thus, while there are numerous combinations of beneficial agents which have been found useful for administration orally or by injection, for example, it is by no means obvious that a particular combination of such agents or other agents could also be safely and effectively administered transdermally.

U.S. Pat. No. 4,816,258 discloses a transdermal delivery system for administering ethinyl estradiol and levonorgestrel, together with a permeation enhancer, as a contraceptive. Levonorgestrel is known to be readily active when taken orally.

However, it has now been found by the present inventors that levonorgestrel, even in the presence of a permeation enhancer such as glycerol monooleate, does not transport across human epidermis in vivo sufficiently to achieve contraceptively effective levels of the drug in the blood from transdermal systems of reasonable or acceptable size.

It has now been seen that ST-1435 acts very differently from levonorgestrel when applied transdermally. ST-1435, which is inactive orally, unpredictably has a greatly increased flux across epidermis in comparison to levonorgestrel, which flux is sufficient when applied transdermally to provide blood drug levels from reasonably sized systems in amounts that produce effective contraception, in marked contrast to levonorgestrel.

Australian patent AU-A-15323/88 discloses a transdermal delivery system for the delivery of estrogens and synthetic gestogens for the treatment of climacteric syndrome (the withdrawal symptoms associated with menopause and caused by estrogen deficiency). The patent makes a general statement that natural gestogens, such as progesterone, do not pass through the skin in amounts sufficient to achieve adequate therapeutic effect using transdermal systems of conventional size, but that synthetic gestogens do have sufficient flux. Levonorgestrel (or d-norgestrel) is named in the patent as a synthetic gestogen which can be used in the transdermal system, and norgestrel and norethisterone-17-acetate are named as preferred synthetic gestogens for use in the system. ST-1435 is not mentioned as a candidate gestogen. It is to be noted here that a markedly greater amount of a gestogen and, consequently, a greater transdermal flux of the drug, is required for effective contraception than is required for treatment of climacteric syndrome. As discussed previously herein, it has been shown that levonorgestrel, the active enantiomer of the preferred gestogen norgestrel, does not, in fact, have a sufficient flux to provide a contraceptively effective plasma level of drug when applied transdermally from a reasonably sized system. Additionally, norethisterone-17-acetate (also known as norethindrone-17-acetate and the only drug for which actual data is presented in the Australian patent) has also been found to have an insufficient transdermal flux from a reasonably sized system to provide effective contraception. These facts show that the broad statement in the Australian patent is not in fact generally true and that sufficient flux of synthetic gestogens, particularly with respect to providing a contraceptive effect, is a continuing problem and cannot be predicted.

Thus, it is by no means obvious that a particular synthetic estogen could be effectively administered transdermally, with or without a permeation enhancer, and especially in an amount sufficient to provide a contraceptive effect. That the gestogen could be delivered in a contraceptively effective amount from a reasonably sized system is especially desired and even less predictable or obvious.

U.S. Pat. No. 4,863,738 discloses glycerol monooleate as a suitable skin permeation enhancer for steroids.

U.S. Pat. No. 4,746,515 discloses glycerol monolaurate as a suitable skin permeation enhancer for steroids.

SUMMARY OF THE INVENTION

An object of the present invention is to provide delivery of contraceptives by means of transdermal devices.

A further object of the invention is to co-administer estrogens and ST-1435 transdermally at contraceptively effective rates.

Another object of the invention is to provide a method for the transdermal administration of estrogens and ST-1435, in combination.

Yet another object of the invention is to co-administer estrogens and ST-1435 at contraceptively effective rates from transdermal systems of reasonable size.

These and other objects have been demonstrated by the present invention which provides a method for the transdermal coadministration of a therapeutically effective amount of an estrogen, such as ethinyl estradiol, and ST-1435, optionally together with a skin permeation-enhancing amount of a suitable permeation a enhancer.

The system of the invention is a transdermal drug delivery device comprising a matrix adapted to be placed in drug- and permeation enhancer-transmitting relation with the skin site. The matrix contains sufficient amounts of a permeation enhancer and of an estrogen and ST-1435, in combination, to continuously coadminister to the skin for a predetermined period of time the drugs and, if included, the permeation enhancer to provide effective contraception. The device is of a reasonable size useful for the application of the drugs and the enhancer to a human body. By "reasonable size", as used herein, is meant a device of conventional size with a base surface area (in contact with the skin site) that is from about 1 $cm^2$ to about 50 $cm^2$, preferably from about 5 $cm^2$ to about 25 $cm^2$. While devices of as large as 200 $cm^2$ can be considered to be of "conventional" size, such large sizes are not generally acceptable to women for use for contraception and therefore are not considered to be of "reasonable" size.

DETAILED DESCRIPTION OF THE INVENTION

This invention utilizes principles of transdermal drug delivery to provide a novel system for effectively administering drugs which can have a contraceptive effect. Particularly, the present invention provides continuous co-administration of an estrogen, such as ethinyl estradiol, and ST-1435 through the skin or mucosa for up to seven days or longer. A suitable permeation enhancer is optionally present together with the drugs. The flux of the drug formulation provided by this invention is sufficient to achieve contraceptively effective blood levels of the estrogen and the ST-1435 from transdermal systems of reasonable size.

Figure 1:
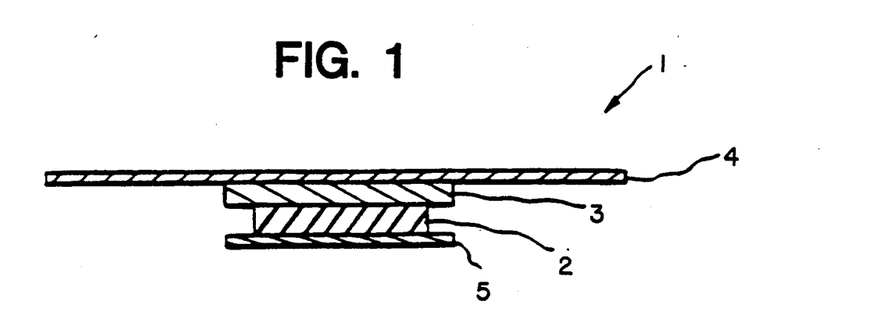
FIG. 1 is a cross-sectional view of one embodiment of a transdermal therapeutic drug delivery device which may be used in accordance with the present invention.
Figure 3:
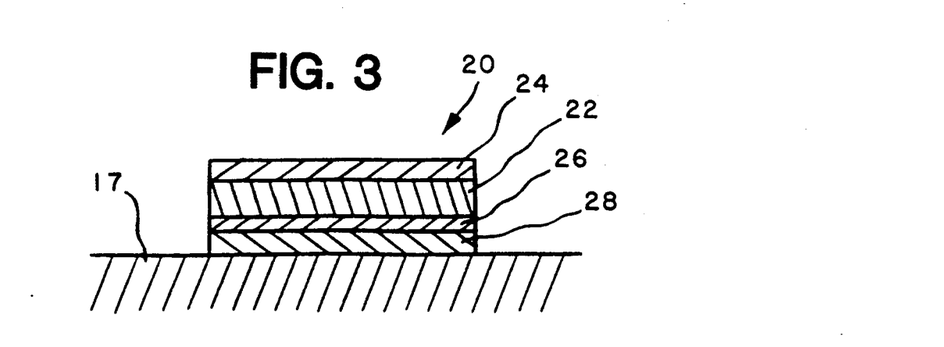
FIG. 3 is a cross-sectional view of yet another embodiment of a transdermal therapeutic drug delivery device which may be used in accordance with this invention.

One embodiment of a transdermal delivery device of the present invention is illustrated in FIG. 1. In FIG. 1, device 1 is comprised of a ST-1435-, estrogen- and permeation enhancer-containing reservoir ("drug reservoir") 2 which is preferably in the form of a matrix containing the drugs and the enhancer dispersed therein. A backing member 3 is provided adjacent one surface of drug reservoir 2. Adhesive overlay 4 maintains the device 1 on the skin and may be fabricated together with, or provided separately from, the remaining elements of the device. With certain formulations, the adhesive overlay 4 may be preferable to an in-line contact adhesive, such as adhesive layer 28 as shown in FIG. 3. This is true, for example, where the drug reservoir contains a material (such as, for example, an oily surfactant permeation enhancer) which adversely affects the adhesive properties of the in-line contact adhesive layer 28. Backing member 3 is preferably slightly larger than drug reservoir 2, and in this manner prevents the materials in drug reservoir 2 from adversely interacting with the adhesive in overlay 4. A strippable or removeable liner 5 is also provided with device 1 and is removed just prior to application of device 1 to the skin.

Figure 2:
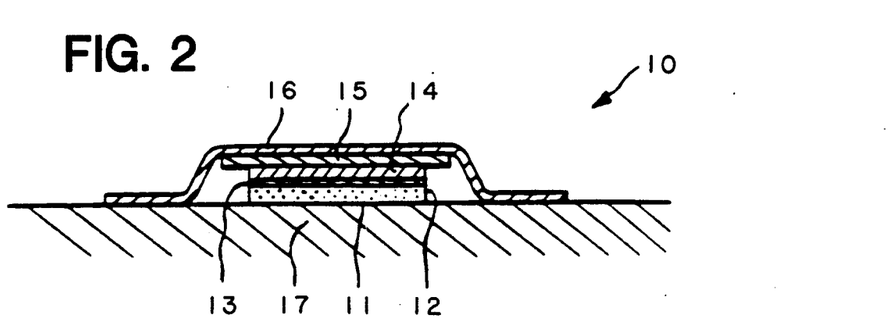
FIG. 2 is a cross-sectional view of another embodiment of a transdermal therapeutic drug delivery device which may be used in accordance with the present invention.

FIG. 2 illustrates another embodiment of the invention, device 10, shown in place upon the skin 17. In this embodiment, the transdermal therapeutic delivery device 10 comprises a multilaminate drug formulation/enhancer reservoir 11 having at least two zones 12 and 14. Zone 12 consists of a drug reservoir substantially as described with respect to FIG. 1. Zone 14 comprises a permeation enhancer reservoir which is preferably made from substantially the same matrix as is used to form zone 12. Zone 14 comprises permeation enhancer dispersed throughout and is substantially free of any undissolved estrogen or ST-1435. A rate-controlling membrane 13 for controlling the release rate of the enhancer from zone 14 to zone 12 is placed between the two zones. A rate-controlling membrane (not shown) for controlling the release rate of the enhancer from zone 12 to the skin may also optionally be utilized and would be present between the skin 17 and zone 12.

The rate-controlling membrane may be fabricated from permeable, semipermeable or microporous materials which are known in the art to control the rate of agents into and out of delivery devices and having a permeability to the permeation enhancer lower than that of zone 12. Suitable materials include, but are not limited to, polyethylene, polyvinyl acetate and ethylene vinyl acetate copolymers.

An advantage of the device described in FIG. 2 is that the drug-loaded zone 12 is concentrated at the skin surface rather than throughout the entire mass of the reservoir 11. This functions to reduce the amount of drugs in the device while maintaining an adequate permeation enhancer supply.

Superimposed over the drug formulation/enhancer reservoir 11 of device 10 is a backing member 15 and an adhesive overlay 16 as described above with respect to FIG. 1. In addition, a strippable liner (not shown) would preferably be provided on the device prior to use as described with respect to FIG. 1 and removed prior to application of the device 10 to the skin 17.

In the embodiments of FIGS. 1 and 2, the carrier or matrix material has sufficient viscosity to maintain its shape without oozing or flowing. If, however, the matrix or carrier is a low viscosity flowable material, the composition can be fully enclosed in a pouch or pocket formed between the backing member and a permeable or microporous skin-contacting membrane, as known to the art from U.S. Pat. No. 4,379,454 (noted above), for example.

An example of a presently preferred transdermal delivery device is illustrated in FIG. 3. In FIG. 3, transdermal delivery device 20 comprises a reservoir 22 containing together the ST-1435, the estrogen and the permeation enhancer. Reservoir 22 is preferably in the form of a matrix containing the drugs and the enhancer dispersed therein. Reservoir 22 is sandwiched between a backing member 24, which is impermeable to both the drugs and the enhancer, and a rate-controlling membrane 26. In FIG. 3, the reservoir 22 is formed of a material, such as a rubbery polymer, that is sufficiently viscous to maintain its shape. If a lower viscosity material is used for reservoir 22, such as an aqueous gel, backing member 24 and rate-controlling membrane 26 would be sealed together about their periphery to prevent leakage. The device 20 adheres to the surface of the skin 17 by means of an in-line contact adhesive layer 28. The adhesive for layer 28 should be chosen so that it is compatible and does not interact with any of the estrogen or ST-1435 or, in particular, the permeation enhancer. The adhesive layer 28 may optionally contain enhancer and/or drugs. A strippable liner (not shown) is normally provided along the exposed surface of adhesive layer 28 and is removed prior to application of device 20 to the skin 17. In an alternative embodiment, the rate-controlling membrane 26 is not present and the reservoir 22 is sandwiched between backing member 24 and adhesive layer 28.

Various materials suited for the fabrication of the various layers of the transdermal devices of FIGS. 1, 2 and 3 are known in the art or are disclosed in the aforementioned transdermal device patents previously incorporated herein by reference.

The matrix making up the ST-1435/estrogen/permeation enhancer reservoir can be a gel or a polymer. Suitable materials should be compatible with ST-1435, the estrogen, the permeation enhancer and any other components in the system. Suitable matrix materials include, without limitation, natural and synthetic rubbers or other polymeric material, thickened mineral oil, or petroleum jelly, for example. The matrix is preferably polymeric and is more preferably an anhydrous polymer. A preferred embodiment according to this invention is fabricated from an ethylene vinyl acetate (EVA) copolymer, of the type described in U.S. Pat. No. 4,144,317, and is preferably selected from those EVAs having a vinyl acetate (VA) content in the range of about 9 to 60%, preferably about 28 to 60% VA. Particularly good results may be obtained using EVA of 40% vinyl acetate content.

In addition to ST-1435, an estrogen and, optionally, a permeation enhancer, the matrix may also contain stabilizers, dyes, pigments, inert fillers, tackifiers, excipients and other conventional components of transdermal delivery devices as are known in the art.

The amounts of the estrogen and of ST-1435 that are present in the therapeutic device, and that are required to achieve a contraceptive effect, depend on many factors, such as the minimum necessary dosage of each drug; the permeability of the matrix, of the adhesive layer and of the rate-controlling membrane, if present; and the period of time for which the device will be fixed to the skin. Since the drugs are to be released over a period of more than one day, there is, in fact, no upper limit to the maximum amounts of the drugs present in the device. The minimum amount of each drug is determined by the requirement that sufficient quantities of drug must be present in the device to maintain the desired rate of release over the given period of application.

The ST-1435 is generally dispersed through the matrix at a concentration in excess of saturation, i.e. at unit activity. The amount of excess is determined by the intended useful life of the system. The drug, however, may be present at initial levels below saturation without departing from this invention. When the estrogen is the natural estrogen 17-$\beta$-estradiol, it is also generally present in the matrix at a concentration in excess of saturation. However, the concentration of a synthetic estrogen, such as ethinyl estradiol, in the matrix is generally in an amount below saturation, as the flux of the estrogen through human epidermis has been found to be proportional to the concentration of estrogen in the drug reservoir.

The permeation enhancer is dispersed through the matrix, preferably at a concentration sufficient to provide permeationenhancing concentrations of enhancer in the reservoir throughout the anticipated administration period.

The permeation enhancer useful in the present invention is selected from those compounds which are compatible with ST-1435 and with the estrogen and which provide enhanced skin permeation to these two drugs when it is administered together with the drugs to the skin of a user. Such permeation enhancers can be selected from, but are not limited to, $C_{2-4}$alcohols such as ethanol and isopropanol, polyethylene glycol monolaurate, polyethylene glycol-3-lauramide, dimethyl lauramide, esters of fatty acids having from about 10 to about 20 carbon atoms, and monoglycerides or mixtures of monoglycerides of fatty acids having a total monoesters content of at least 51% where the monoesters are those with from 10 to 20 carbon atoms. Diglycerides and triglycerides of fatty acids, or mixtures thereof, are also included. Fatty acids are, for example, lauric acid, myristic acid, stearic acid, oleic acid, linoleic acid and palmitic acid. Monoglyceride permeation enhancers include glycerol monooleate, glycerol monolaurate and glycerol monolinoleate, for example. In a preferred embodiment, the permeation enhancer is polyethylene glycol-3-lauramide (PEG-3-LR), glycerol monooleate (GMO), glycerol monolinoleate or glycerol monolaurate (GML), more a preferably glycerol monooleate.

The system of the invention contains a drug formulation comprising an estrogen and ST-1435.

The term "estrogen" includes both the natural 17-$\beta$-estradiol and the semi-synthetic estrogen derivatives such as the esters of natural estrogen, such as estradiol-17-$\beta$-enanthate, estradiol-17-$\beta$-valerate, estradiol-3-benzoate, estradiol-17-$\beta$-undecenoate, estradiol-16,17-hemisuccinate or estradiol-17-$\beta$-cypionate; 17-alkylated estrogens, such as ethinyl estradiol, ethinyl estradiol-3-isopropylsulphonate, quinestrol, mestranol or methyl estradiol; and non-steroidal compounds having estrogen activity, such as diethylstilbestrol, dienestrol, clomifen, chlorotrianisen or cyclofenil. The drug formulation of the invention preferably contains 17-$\beta$-estradiol or ethinyl estradiol as the estrogen.

In the present invention, ST-1435 and an estrogen, such as ethinyl estradiol, are delivered, in combination, at a contraceptively effective rate (that is, a rate that provides effective contraception) and the permeation enhancer is delivered at a permeation-enhancing rate (that is, a rate that provides increased permeability of the application site to both the estrogen and ST-1432) for a predetermined time period.

The required transdermal flux for effective contraception as provided by this invention is at least 10 $\mu$g/day of ethinyl estradiol or 50 $\mu$g/day of 17-$\beta$-estradiol and at least 20 $\mu$g/day of ST-1435. For a 10 $cm^2$ device, these daily flux values translate to be at least 0.04 $\mu g/cm^2/hr$ for ethinyl estradiol or 0.2 $\mu g/cm^2/hr$ for 17-$\beta$-estradiol and at least 0.08 $\mu g/cm^2/hr$ for ST-1435.

The backing member useful in the present invention may be chosen from materials that are occlusive or non-occlusive and they may be flexible or non-flexible. By "non-occlusive" is meant that the material is permeable to water vapor and/or oxygen. In addition, the backing material is impermeable to the ST-1435, the estrogen and the permeation enhancer. Materials suitable for use as a backing member are known in the art and exemplary materials include acrylonitrile, cellophane, cellulose acetate, cellulosics, ethylcellulose, ethylene vinyl alcohol, ethylene vinyl acetate, plasticized vinylacetate-vinylchloride copolymers, polyethylene terephthalate, nylon, rayon, polyethylene, polypropylene, polyvinyl alcohol, polyvinyl chloride, polyvinylidene chloride, polyester, polycarbonate, polystyrene, polyurethane, flexible fibrous materials such as paper and cloth, aluminized plastics and aluminum foil, and mixtures, copolymers and multilaminates thereof.

A preferred embodiment of the present invention is a monolith such as that illustrated in FIG. 3 (either with or without the rate-controlling membrane 26) wherein reservoir 22 comprises, by weight, 50–90% polymer (preferably EVA), 0.01–5% estrogen (preferably ethinyl estradiol), 0.1–20% ST-1435, and 10–50% permeation enhancer (preferably GMO). The in-line adhesive layer 28 contains an adhesive which is compatible with the permeation enhancer.

The devices of this invention can be designed to effectively deliver an estrogen and ST-1435 in a therapeutically effective amount for an extended time period of up to seven days or longer. By "therapeutically effective" amount is meant an amount that provides a desired therapeutic effect. Seven days is generally the maximum time limit for application of a single device because the skin site is adversely affected when occluded for a period greater than seven days. When a non-occlusive backing material is used in the device, adverse effects may not occur or may occur at a later time so that a single device may be applied for a period longer than seven days. The drug delivery must be continuous in order to provide effective contraception. Therefore, when one device has been in place on the skin for its effective time period, it is replaced with a fresh device, preferably on a different skin site. For example, for a seven-day device, maintenance would involve replacing the device every seven days with a fresh device and continuing said replacement for as long as contraception was desired. In an alternative method of obtaining effective contraception, it may be desired to apply devices containing ST-1435 and estrogen for a period of three weeks, followed by application for one week of a device as disclosed herein but containing only the estrogen.

The transdermal therapeutic devices of the present invention are prepared in a manner known in the art, such as by those procedures, for example, described in the transdermal device patents listed previously herein.

The following examples are offered to illustrate the practice of the present invention and are not intended to limit the invention in any manner.

The devices for Examples 1 and 2 are prepared as follows:

A. Formulation Without Permeation Enhancer

A control formulation containing 2 wt % (weight percent) ST-1435 in a matrix of EVA 40 was prepared by dissolving the ST-1435 and EVA 40 in methylene chloride. The solution was poured onto a FCD/polyester release liner to evaporate. The dried material was pressed to 5 mil (ca. 0.1 mm) thickness between two sheets of FCD/polyester release liner at 75° C. The resulting film was heat-laminated to an impermeable backing (Medpar ® or Scotchpak ®, for for example), and 1.6 and 0.97 $cm^2$ discs were punched or die-cut from the laminate.

B. Formulations Containing Permeation Enhancers

Formulations containing various ST-1435 concentrations, various permeation enhancers (GMO, polyethylene glycol-3-lauramide (PEG-3-LR) and GML), and various permeation enhancer concentrations in a matrix of EVA 40 were prepared by dissolving the necessary components in methylene chloride and following the same procedures as in A, above.

The GMO used was Myverol ® 1899K glycerol monooleate ("M-GMO") (Eastman Chemical Products), having a glycerol monooleate content of 61% and a total monoesters content of 93%.

C. Devices with In-line Adhesive

Each of the drug matrix/impermeable backing laminates were divided in half, and one-half of each were laminated to 3M acrylate transfer adhesive MSP 32589 (1.6 mil; an acrylate adhesive with 2–5% acid functionality; 3M). Before testing, each final laminate was equilibrated for at least 5 days to allow the enhancer and the drugs to partition into the contact adhesive. The edges of the devices with in-line adhesive were masked with polyester tape so that the drug reservoir edges were not exposed to the epidermis or solutions when they were tested.

EXAMPLE 1

The in vitro transdermal ST-1435 fluxes through the epidermis of human skin donors A, B and C from devices containing 2.5 wt % ST-1435 and either no permeation enhancer or the permeation enhancer M-GMO, PEG-3-LR or GML at 30 wt % loading were compared, with and without an in-line adhesive.

For each device tested, the release liner was removed and the drug-releasing surface was placed against the stratum corneum side of a disc of human epidermis which had been blotted dry just prior to use. The excess epidermis was wrapped around the device so that none of the device edge was exposed to the receptor solution. The device covered with epidermis was attached to the flat side of the Teflon holder of a release rate rod using nylon netting and nickel wire. The rods were reciprocated in a fixed volume of receptor solution (5% ethanol in distilled water). The entire receptor solution was changed at each sampling time. The temperature of the receptor solution in the water bath was maintained at 37° C. Each formulation was tested twice with each skin donor.

A summary of the results, as the average transdermal ST-1435 flux in $\mu g/cm^2/hr$ over 0–4 days (for donors A and B) or 0–3 days (for donor C), is given in Table I below.

TABLE I

| Permeation Enhancer | Donor A | Donor B | Donor C |
|---|---|---|---|
| None | | | |
| without adhesive | 0.55 | 0.55 | 0.16 |
| with adhesive | — | — | 0.11 |
| M-GMO | | | |
| without adhesive | 1.30 | 4.10 | 0.70 |
| with adhesive | 0.94 | 2.75 | 0.67 |
| GML | | | |
| without adhesive | 2.06 | 4.15 | 1.18 |
| with adhesive | 1.55 | 1.95 | 0.53 |
| PEG-3-LR | | | |
| without adhesive | 1.22 | 1.57 | 0.58 |
| with adhesive | 0.98 | 1.32 | 0.28 |

EXAMPLE 2

The in vitro transdermal ST-1435 fluxes through the epidermis of human skin donors A, B and C from devices containing 30 wt % M-GMO and various loadings of ST-1435 were tested, following the procedures of Example 1. A summary of the results, as the average transdermal ST-1435 flux in $\mu g/cm^2/hr$ over 0–4 days (for donors A and B) or 0–3 days (for donor C), is given in Table II below.

TABLE II

| Wt % ST-1435 | Donor A | Donor B | Donor C |
|---|---|---|---|
| 2.6 wt % | | | |
| w/o adhesive | 1.30 | 4.10 | 0.70 |
| with adhesive | 0.94 | 2.75 | 0.67 |
| 4.1 wt % | | | |
| w/o adhesive | 1.69 | 4.43 | 1.00 |
| with adhesive | 1.45 | 3.36 | 0.82 |
| 7.8 wt % | | | |
| w/o adhesive | 1.84 | 4.77 | 0.67 |
| with adhesive | 1.29 | — | 0.64 |

EXAMPLE 3

A transdermal therapeutic device as described with respect to FIG. 3 (but without the rate-controlling membrane) for the administration of 17-β-estradiol and ST-1435 was formulated as s follows.

A formulation containing 4 wt % ST-1435, 2 wt % 17-β-estradiol and 30 wt % Myverol ® 1899K (glycerol monooleate) in a matrix of EVA 40 (64 wt %) was prepared by dissolving all of the components (not all of the 17-β-estradiol was dissolved) in methylene chloride. The mixture was poured onto FCD/polyester release liner and the solvent was allowed to evaporate off. The dried material was pressed into a film of 5 mil (approx. 0.1 mm) thickness between two sheets of FCD/polyester release liner at 80° C. Two films were made and both were laminated to a cloth backing material (spunlace polyester, SL-PET, 1.3 oz/yd²; Chickopee). One of the drug matrix/cloth backing laminates was laminated, on the surface away from the backing, to acrylate transfer adhesive MSP 32589 (3M; 1.6 mil layer). The laminate with adhesive was equilibrated for at least five days to allow the enhancer and the drugs to partition into the adhesive before being tested.

Figure 4:
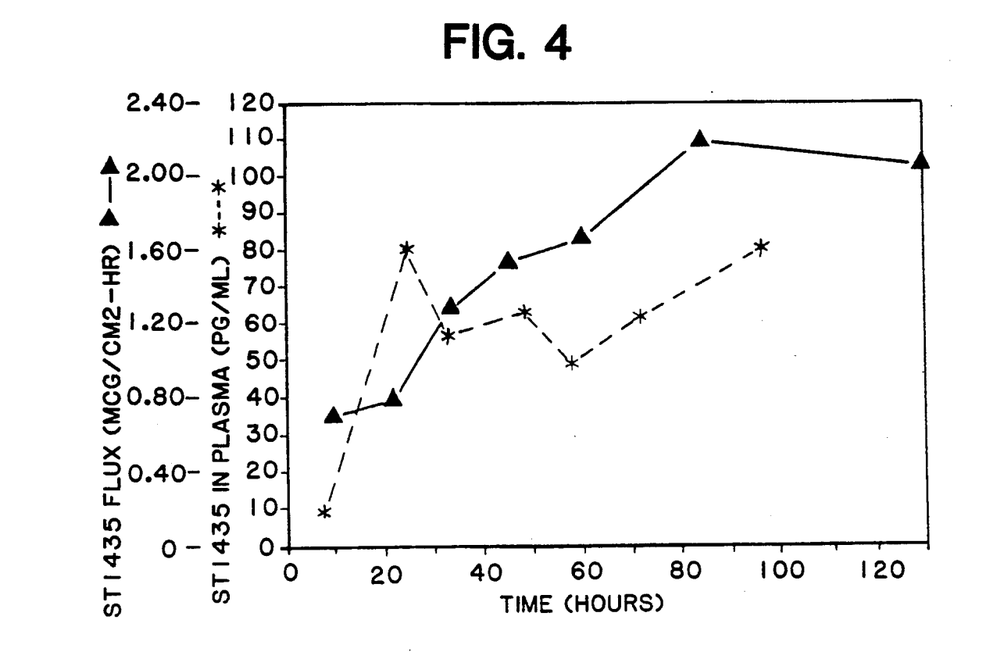
FIG. 4 shows graphically the in vitro transdermal flux and the in vivo plasma levels of ST-1435 delivered from a transdermal device according to this invention.
Figure 5:
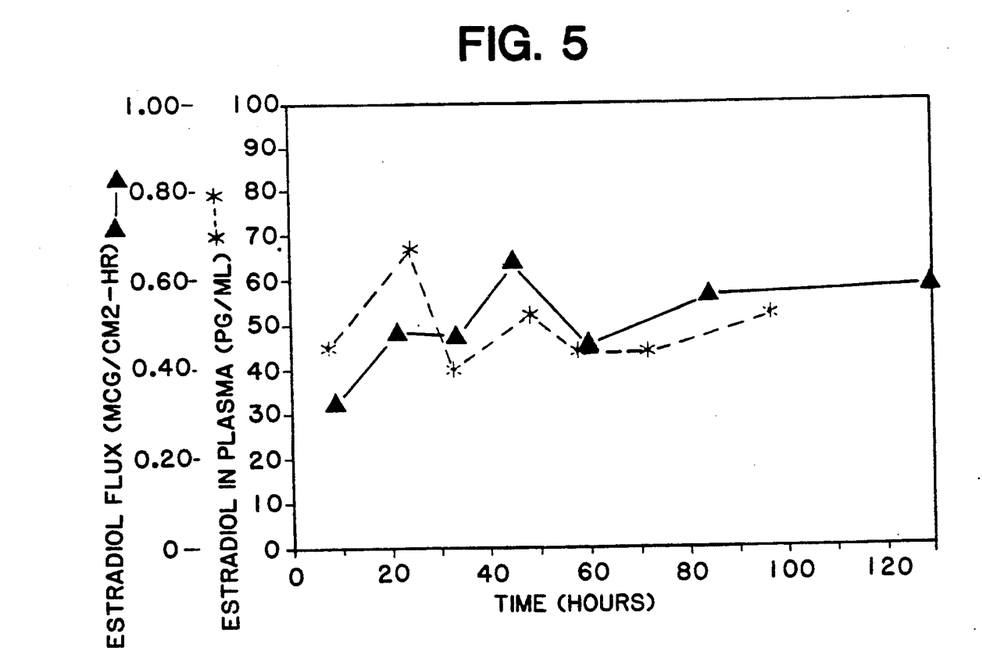
FIG. 5 shows graphically the in vitro transdermal flux and the in vivo plasma levels of 17-$\beta$-estradiol delivered from a transdermal device according to this invention.

The in vitro skin flux of the 17-β-estradiol and the ST-1435 from the device through human cadaver epidermis (one donor, n=3) was measured at various time points, following the procedures of Example 1. The average flux in vitro of the ST-1435 is shown in FIG. 4 (indicated by triangles) and the average flux of the estradiol is shown in FIG. 5 (indicated by triangles).

The laminate with adhesive was also tested in vitro against a control device having no in-line adhesive and having an impermeable backing. The control was a device comprising a formulation containing 4 wt % ST-1435 and 30 wt % Myverol 1899K in an EVA 40 matrix, the device being prepared in the same manner as described above except that the backing was an impermeable film (Scotchpak ®). The average transdermal ST-1435 flux through epidermis, averaged over 96 hours, was 1.60 mcg/cm$^2$ hr from the laminate with the cloth backing and was 1.48 mcg/cm$^2$ hr from the laminate with the Scotchpak backing.

EXAMPLE 4

Devices prepared as in Example 3 were placed on two human subjects, and the level of 17-β-estradiol and ST-1435 in the blood serum of the subjects was measured at various time points. The serum level (as an average of the two subjects) of ST-1435 is shown in FIG. 4 (indicated by asterisks) and of the estradiol, in FIG. 5 (indicated by asterisks).

EXAMPLE 5

The in vitro transdermal flux of ST-1435 was compared with that of levonorgestrel as follows.

Figure 6:
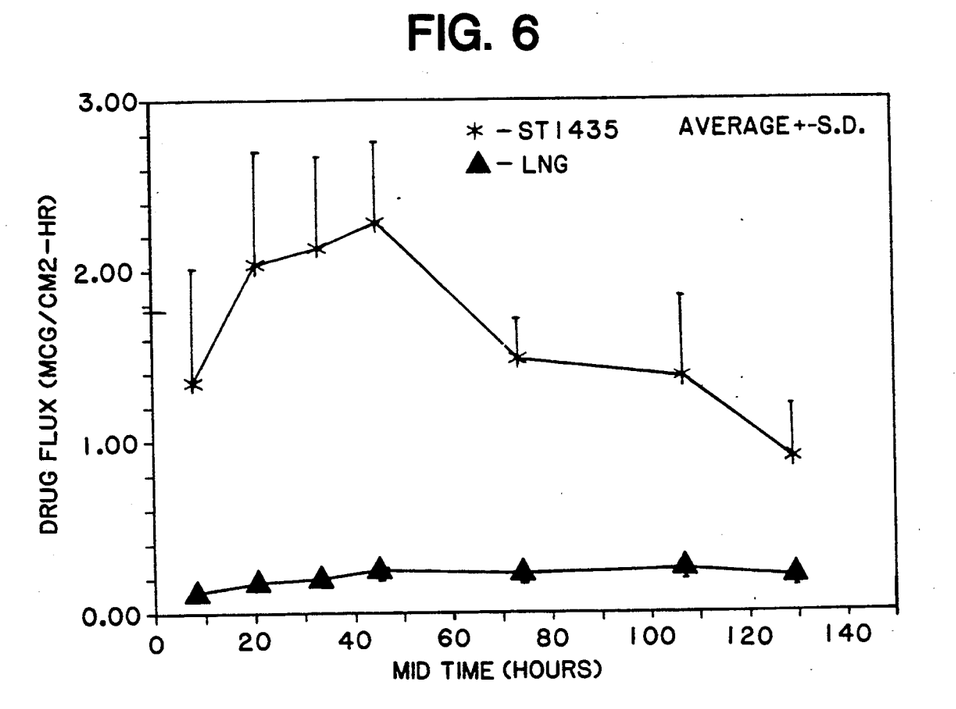
FIG. 6 is a graph showing the comparative in vitro transdermal fluxes of ST-1435 and levonorgestrel from transdermal delivery devices.

ST-1435-containing transdermal devices were prepared comprising ST-1435, in an amount greater than saturation, and 30 wt % Myverol 18-99K in an EVA 40 matrix and with an in-line MSP 32589 adhesive layer. Levonorgestrel-containing transdermal devices were prepared comprising levonorgestrel, in an amount greater than saturation, and 25 wt % Myverol 18-99K in an EVA 40 matrix and with an in-line adhesive layer of MSP 121388 acrylate adhesive (with 2-5% acid functionality; 3M). Each device was 1.6 cm$^2$ in size. Three of each of the ST-1435- and the levonorgestrel-containing devices were placed on the skin of each of three human cadaver donors. The flux (as an average of the three donors) of each of the two drugs through the epidermis was determined at various time points, following the procedures of Example 1. The results, shown in FIG. 6, indicate that levonorgestrel (L-NG) has a very low flux through human cadaver epidermis, while that of ST-1435 is substantially greater.

This invention has been described in detail with particular reference to certain preferred embodiments thereof, but it will be understood that variations and modifications can be effected within the spirit and scope of the invention.

What is claimed is:

1. A composition of matter for the transdermal administration of a drug formulation comprised of an estrogen and ST-1435, the composition comprising, in combination, an amount of the drug formulation to deliver at least 10 g/day of estrogen and at least 20 μg/day of ST-1435 and a skin permeation-enhancing amount of a suitable permeation enhancer, the permeation enhancer being selected from $C_{2-4}$ alcohols, polyethylene glycol monolaurate, polyethylene glycol-3-lauramide, dimethyl lauramide, esters of fatty acids having from about 10 to about 20 carbon atoms, diglycerides of fatty acids, triglycerides of fatty acids, and monoglycerides or mixtures of monoglycerides of fatty acids having a total monoesters content of at least 51% where the monoesters are those with from 10 to 20 carbon atoms.

2. A composition according to claim 1 wherein the estrogen is ethinyl estradiol.

3. A composition according to claim 1 wherein the permeation enhancer is a monoglyceride or mixture of monoglycerides of fatty acids with a total monoesters content of at least 51%.

4. A composition according to claim 3 wherein the permeation enhancer is glycerol monooleate, glycerol monolinoleate, or glycerol monolaurate.

5. A composition according to claim 1 wherein the estrogen is ethinyl estradiol and the permeation enhancer is glycerol monooleate.

6. A method for the transdermal administration of a drug formulation comprised of an estrogen and ST-1435, which method comprises:
   (a) administering the drug formulation at a rate of at least 10 μg/day of estrogen and at least 20 μg/day of ST-1435 to an area of skin, the area being of from about 1 cm$^2$ to about 50 cm$^2$; and
   (b) simultaneously administering a suitable permeation enhancer to the area of skin at rates which are sufficient to substantially increase the permeability of the area to the drug formulation, the permeation enhancer being selected from $C_{2-4}$ alcohols, polyethylene glycol monolaurate, polyethylene glycol-3-lauramide, dimethyl lauramide, esters of fatty acids having from about 10 to about 20 carbon atoms, diglycerides of fatty acids, triglycerides of fatty acids, and monoglycerides or mixtures of monoglycerides of fatty acids having a total monoesters content of at least 51% where the monoesters are those with from 10 to 20 carbon atoms.

7. A method according to claim 6 wherein the estrogen is ethinyl estradiol.

8. A method according to claim 6 wherein the permeation enhancer is a monoglyceride or mixture of monoglycerides of fatty acids with a total monoesters content of at least 51%.

9. A method according to claim 8 wherein the permeation enhancer is glycerol monooleate, glycerol monolinoleate or glycerol monolaurate.

10. A method according to claim 6 wherein the estrogen is ethinyl estradiol and the permeation enhancer is glycerol monooleate.

11. A method for providing contraception to a woman, which method comprises:
   (a) administering a drug formulation comprised of an estrogen and ST-1435 at a rate of at least 10 μg/day of estrogen and at least 20 μg/day of ST-1435 to an area of the woman's skin, the area being of from about 1 cm$^2$ to about 50 cm$^2$; and
   (b) simultaneously administering a suitable permeation enhancer to the area of skin at rates which are sufficient to substantially increase the permeability of the area to the drug formulation, the permeation enhancer being selected from $C_{2-4}$ alcohols, polyethylene glycol monolaurate, polyethylene glycol-3-lauramide, dimethyl lauramide, esters of fatty acids having from about 10 to about 20 carbon atoms, diglycerides of fatty acids, triglycerides of fatty acids, and monoglycerides or mixtures of monoglycerides of fatty acids having a total monoesters content of at least 51% where the monoesters are those with from 10 to 20 carbon atoms.

12. A method according to claim 11 wherein the estrogen is ethinyl estradiol.

13. A method according to claim 11 wherein the permeation enhancer is a monoglyceride or mixture of monoglycerides of fatty acids with a total monoesters content of at least 51%.

14. A method according to claim 13 wherein the permeation enhancer is glycerol monooleate, glycerol monolinoleate or glycerol monolaurate.

15. A method according to claim 11 wherein the estrogen is ethinyl estradiol and the permeation enhancer is glycerol monooleate.

16. A device for the transdermal administration of a drug formulation comprised of an estrogen and ST-1435, which device is of a size of from about 1 cm$^2$ to about 50 cm$^2$ and comprises:

(a) a reservoir comprising a matrix containing a contraceptively effective amount of the drug formulation to deliver at least 10 μg/day of estrogen and at least 20 μg/day of ST-1435 and a skin permeation-enhancing amount of a suitable permeation enhancer, the permeation enhancer being selected from $C_{2-4}$alcohols, polyethylene glycol monolaurate, polyethylene glycol-3-lauramide, dimethyl lauramide, esters of fatty acids having from about 10 to about 20 carbon atoms, diglycerides of fatty acids, triglycerides of fatty acids, and monoglycerides or mixtures of monoglycerides of fatty acids having a total monoesters content of at least 51% where the monoesters are those with from 10 to 20 carbon atoms;

(b) a backing on the skin-distal surface of the reservoir; and (c) means for maintaining the reservoir in estrogen, ST-1435 and permeation enhancer-transmitting relation with the skin.

17. A device according to claim 16 wherein the estrogen is ethinyl estradiol.

18. A device according to claim 16 wherein the permeation enhancer is a monoglyceride or mixture of monoglycerides of fatty acids with a total monoesters content of at least 51%.

19. A device according to claim 18 wherein the permeation enhancer is glycerol monooleate, glycerol monolinoleate or glycerol monolaurate.

20. A device according to claim 16 wherein the estrogen is ethinyl estradiol, the permeation enhancer is glycerol monooleate and the matrix comprises ethylene vinyl acetate copolymer having from about 9 to 60% vinyl acetate.

21. A device according to claim 20 wherein the means for a maintaining the reservoir in relation with the skin comprises an in-line adhesive layer on the skin-proximal surface of the reservoir.

* * * * *

UNITED STATES PATENT AND TRADEMARK OFFICE
CERTIFICATE OF CORRECTION

PATENT NO. : 5,198,223
DATED : March 30, 1993
INVENTOR(S) : Robert M. Gale, Diane E. Nedberge, and Linda E. Atkinson It is certified that error appears in the above-identified patent and that said Letters Patent is hereby corrected as shown below:

On title page, at [*], line 2, delete "Jun. 6" and replace it with --Jun. 16--.

Column 11,
Claim 1, line 5, delete "10 g/day" and replace it with --10 ug/day--.

Signed and Sealed this

Seventh Day of December, 1993

Attest:

BRUCE LEHMAN

Attesting Officer

Commissioner of Patents and Trademarks